United States Patent [19]

Schmidt

[11] Patent Number: 5,517,546
[45] Date of Patent: May 14, 1996

[54] METHOD OF AND DEVICE FOR POSITIONING AN X-RAY CASSETTE

[75] Inventor: Manfred Schmidt, Schrobenhausen, Germany

[73] Assignee: Agfa-Gevaert Aktiengesellschaft, AG, Leverkusen, Germany

[21] Appl. No.: 519,800

[22] Filed: Aug. 28, 1995

[30] Foreign Application Priority Data

Sep. 30, 1994 [DE] Germany .................... 44 35 112.7

[51] Int. Cl.⁶ .................................................. A61B 6/08
[52] U.S. Cl. .................................. 378/206; 378/205
[58] Field of Search ................................. 378/205, 206

[56] References Cited

U.S. PATENT DOCUMENTS 5,241,578  8/1993  MacMahon .................. 378/206

FOREIGN PATENT DOCUMENTS 038179  6/1993  European Pat. Off. .
2608452  9/1977  Germany .
8230456  2/1983  Germany .

OTHER PUBLICATIONS

Laser Alignment System for High-Quality Portable Radiography, H. MacMahon, MD, Nicholas J. Yasillo & Michael Carlin, RT, Radiographics 1992; 12:111–120.

Primary Examiner—Craig E. Church
Attorney, Agent, or Firm—Furgang & Milde

[57] ABSTRACT

A method of, and a device for positioning an X-ray cassette (5 or 10) in relation to a source (1) of X-rays that emits radiation in a specific preferred direction (A). Another beam of radiation is emitted parallel to that direction at a specific distance (d) therefrom. The other beam is intercepted by a positioning device (20) secured to the cassette. The device produces a signal as long as the angle of incidence of the other beam does not exceed a specific threshold angle (θ) with respect to the normal to the cassette.

11 Claims, 4 Drawing Sheets

METHOD OF AND DEVICE FOR POSITIONING AN X-RAY CASSETTE

BACKGROUND OF THE INVENTION

The present invention concerns a method of and device for positioning an X-ray cassette in relation to an X-ray source.

The source of the X-rays employed for diagnostic purposes in emergency rooms in particular is mounted on a mobile structure. To take an X-ray picture the structure is moved to the vicinity of the patient's examining table. The patient to be X-rayed is then usually lifted by the emergency-room personnel and a cassette is slid under him or her. The cassette contains either a conventional X-ray film or an imaging plate containing stimulable elements such as a phosphor or fluorine. To make the exposure the source is positioned above the patent as precisely as possible in relation to the cassette. Once the picture has been taken, the cassette is removed from beneath the patient and the film or plate is removed from the cassette for processing. The conventional X-ray films are developed conventionally and the imaging plates are excited point by point by a beam of light, usually a laser. The stimulated light is sensed electro-optically, generating graphics signals that can be further processed digitally in a computer.

An X-ray cassette can be positioned in relation to a beam of X-rays generated by an X-ray source by means of a primary-radiation diaphragm as described in the European Patent No. 0,381,795. The diaphragm is mounted on an arm extending outward from the source. The diaphragm generates an apparent reticle that can be oriented with respect to a justification field. The justification field is accommodated in a compartment with marks that must be brought into coincidence with the reticle. The cassette itself is inserted into the compartment once the justification has been carried out, and the compartment is advanced below the patient table in a special cart.

One drawback of this approach is that it requires a relatively complicated cart to accommodate the cassette. The approach also requires special tables, which are not widely available and which are manufactured only in small quantities, which adds to the expense.

SUMMARY OF THE INVENTION

The object of the present invention is to provide a relatively simple method and apparatus to very precisely position X-ray cassettes in relation to an X-ray source without excessive expenditure.

This object, as well as other objects which will become apparent in the discussion that follows, are achieved, in accordance with the present invention, by a method and apparatus for intercepting the secondary beam with a positioning device secured to the cassette and indicating whether the angle of incidence of the secondary beam on the positioning device exceeds a specific threshold angle (θ) with respect to the normal to the cassette.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
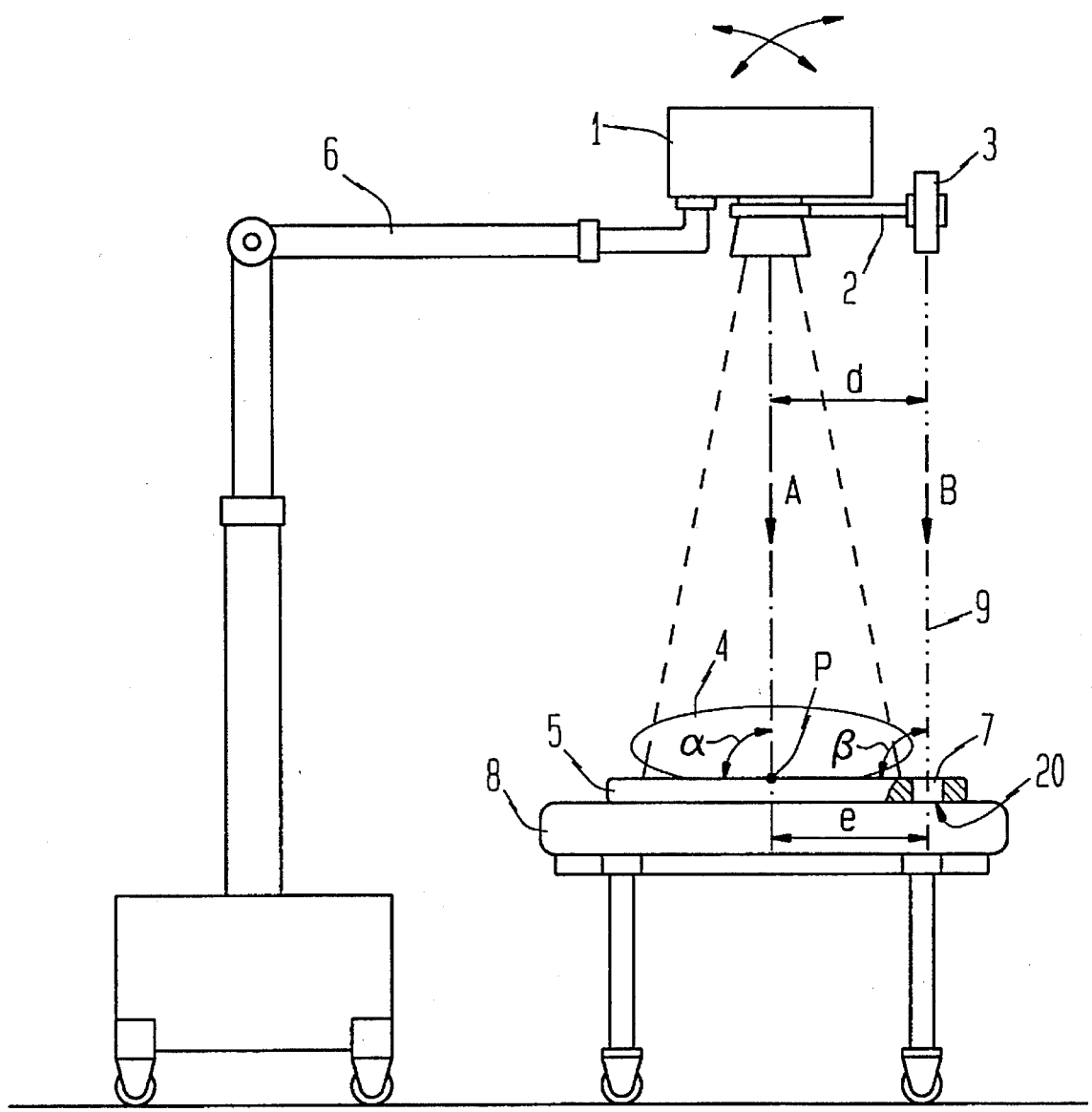
FIG. 1 illustrates mobile X-ray apparatus of the type to which the present invention relates.

FIG. 1 illustrates mobile X-ray apparatus. A source 1 of X-rays is positioned on an structure 6 above a patient examining table 8. Source 1 emits a cone of radiation. The preferred direction, the axis A of the cone, is intercepted by a cassette holder 5 at an angle of incidence α of 90° with respect to the surface of the cassette. The dose is highest along axis A, which extends through a patient 4 lying on the table 8. The cassette holder 5 has been slid under the region of patient 4 to be radiographed. The holder 5 accommodates an X-ray sensitive medium, either a conventional film or a stimulable imaging plate for example. A laser 3 is mounted on a telescoping arrangement 2 attached to the structure 6. The laser 3 swings in at least two directions along with the X-ray source 1. The distance d between laser 3 and X-ray source 1 can be varied by adjusting the length of the telescope. The laser 3 emits a secondary beam 9 in the direction indicated by the arrow B, paralleling the preferred direction A of the X-rays. The laser 3 can be a commercially available helium-neon laser speaker's pointer emitting light at a wavelength of 633 nm. It can be powered with the same electricity that powers the X-ray source 1 or by its own battery.

The edge of the holder 5 is positioned near where the laser light beam 9 is intercepted by the table 8. The holder 5 accommodates a positioning device 7 that detects the light emitted by the laser and generates a visible or audible signal when the light shines directly perpendicular to the surface of the holder 5. The device 7 accordingly acts as a targeting protractor. The distance e between the device 7 and a point P on the holder 5 where the holder is intersected by the axis A equals the distance d between laser 3 and X-ray source 1.

Figure 2:
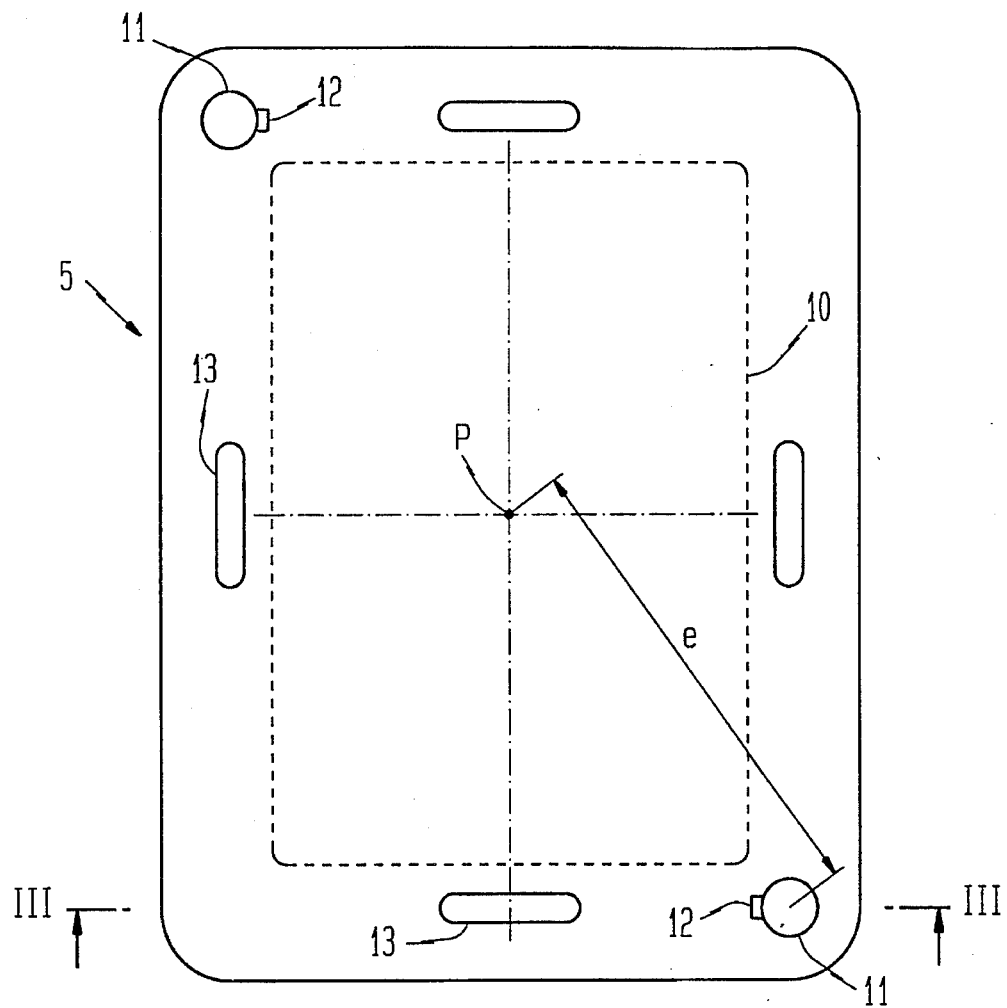
FIG. 2 illustrates a holder for X-ray cassettes, incorporating a positioning device in accordance with the present invention.

FIG. 2 is a top view of the cassette holder 5. It has finger grips 13 on all four sides for positioning the holder under a patient and withdrawing it after the exposure without undue exertion. There are accommodations 11 at two opposite corners of the holder 5 for the positioning device 7. The positioning device 7 can be permanently or temporarily secured in accommodations 11. Slots 12 allow the device 7 to be positioned in a particular orientation to the holder 5 as a whole.

Figure 3:
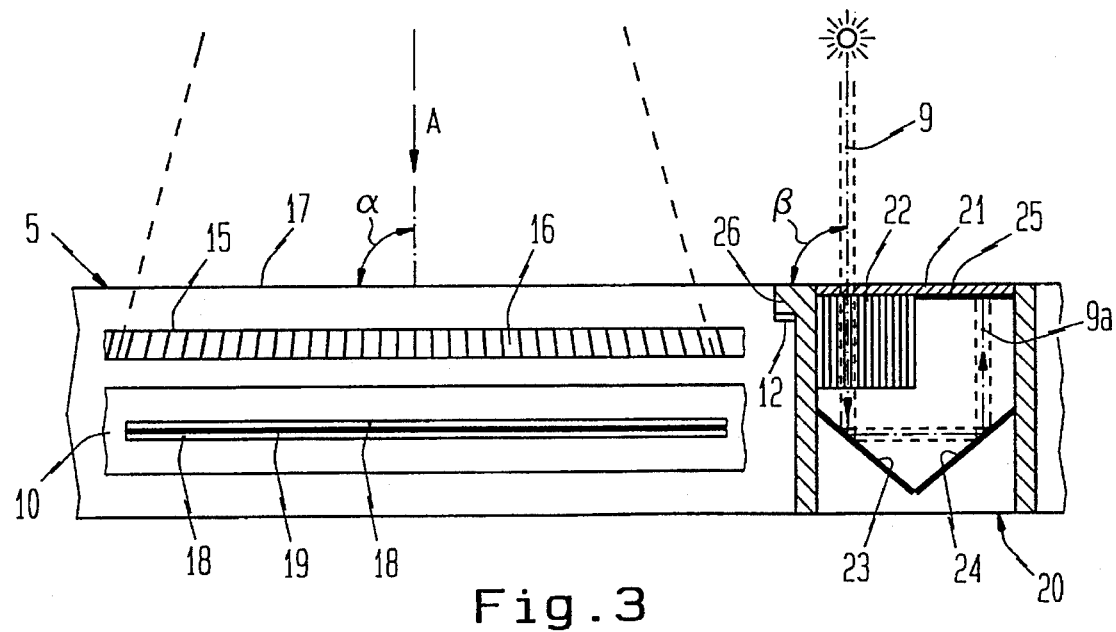
FIG. 3 is a section through the holder taken along the line III—III in FIG. 2.

Details of the positioning device 7 will be evident from the cross-sectional view in FIG. 3.

The X-ray cassette holder 5 employed in accordance with the present invention is described in detail in the commonly-owned German Patent Application No. P 44 27 783.0 and corresponding U.S. Patent application Ser. No. 08/503,106 filed Jul. 17, 1995. The holder removably accommodates a conventional X-ray film cassette 10 of the type disclosed in the U.S. Pat. No. 4,637,043.

As will be evident from FIG. 3, the top of holder 5 accommodates a scatter grid 15 for use in focusing the X-ray beam. The partitions 16 in the scatter grid 15 near the center of holder 5 parallel the axis A (the preferred direction) of the X-rays. Near the edges of the holder, on the other hand, they are aligned with the cone of radiation and slope toward that axis. Accordingly, when the holder 5 is ideally positioned, the partitions will always parallel the beam of X-rays.

Scatter grids are well known. They are used to intercept any stray X-rays deflected toward the patient's body. They essentially comprise substantially parallel and adjacent partitions of lead. How much scattered radiation is absorbed by the grid depends on the "shaft ratio", which is the ratio of the distance between partitions to their length. Some scatter grids have absolutely parallel partitions and can be employed for applications where the beams are not focused.

Accommodated in the holder 5 is a cassette 10 of the type disclosed in the German Patent No. 3,609,527. Such cassettes comprise a top and bottom attached together by a hinge. They can be opened and closed about the hinge. They can be mechanically and automatically loaded and unloaded. Sheets 18 of intensifier screen are positioned over their inner surfaces, with an X-ray film 19 between them. Instead of an X-ray film and intensifier screen, images can be produced on a known, stimulable imaging plate. It is important for satisfactory X-ray imaging that the scattered radiation be absorbed by the scatter grid while the direct radiation travels straight through it without impediment, paralleling the partitions, that is. It is also essential for the direct radiation to impact the cassette or intensifying screens 18 perpendicularly. The X-ray film 19 in the cassette 10 accordingly parallels the surface 17 of holder 5 so that the direct radiation will travel along axis A and shine directly onto surface 17, or more particularly on the intensifying screens 18.

A positioning device 20 according to the present invention comprises a window 21 of transparent plastic or glass integrated flush into surface 17 of the holder 5. The secondary beam 9 passes through the window 21 and enters the positioning device 20 at an angle of incidence $\beta=\alpha$ of 90°. Inside the positioning device 20, the beam is directed onto a reflective surface 23 through light channels 22. The reflective surface 23 slopes at an angle of 45° to the surface of window 21 thus deflecting the beam by and angle of 90°. It subsequently impinges on another reflective surface 24 perpendicular to reflective surface 23 and is deflected another 90°. It is finally intercepted by a matte-surfaced disk 25.

The light channels 22 parallel the central partitions 16 in the scatter grid 15. For this purpose guide 26 projecting out of the edge of positioning device 20 engages a groove 12 in the holder 5.

Figure 4A:
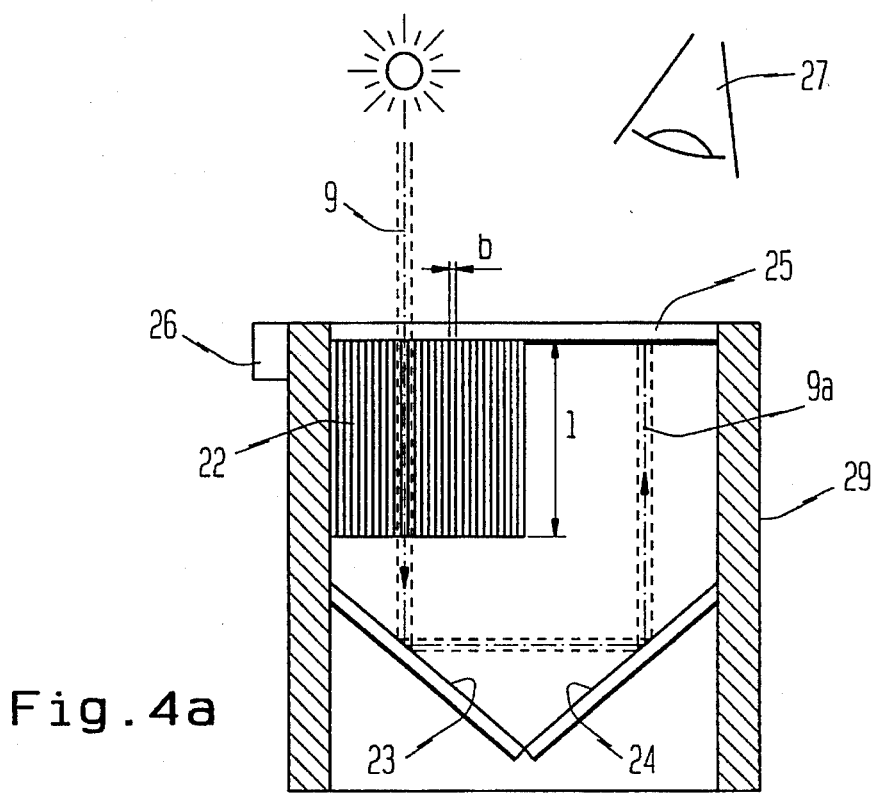
FIGS. 4a, 4b and 4c illustrate preferred embodiments of the cassette-positioning device according to the present invention.

FIG. 4a illustrates a preferred embodiment of the positioning system 20 in detail. Although the light channels 22 conduct light, their inner surfaces are matte black. Light that is not substantially parallel to the channels and does not, therefore, pass straight through the window 21, will be absorbed by the inner surfaces of light channels 22. This absorption can be augmented by coating the channel walls with velvet. The parallelism between the light channels and the angle of incidence of the secondary beam may deviate from the central longitudinal axes of the channels by no more than a threshold angle $\theta$ that depends on the channels' shaft ratio, whereby $$tan\theta=b/l,$$

where b is the available width of the channel and l is its length.

When the holder 5 is correctly positioned, the secondary beam 9 will travel as illustrated in FIG. 4a. It will be reflected onto matte-surfaced disk 25 by reflective surfaces 23 and 24. An observer 27 will perceive the reflected beam 9a as a signal in the disk. When, on the other hand, the holder 5 is not correctly positioned—that is, when its surface is not perpendicular to the axis A—the reflected beam 9a will become displaced within the area of matte-surfaced disk 25. When the threshold angle $\theta$ is exceeded, beam 9 will finally be absorbed inside light channels 22. The partitions between the light channels 22 will accordingly block the beam. An observer 27 will therefore perceive no signal on the matte-surfaced disk 25 when the holder 5 is incorrectly positioned. Inside the positioning device 20, lateral surfaces 29 are coated with black plush to absorb scattered radiation.

Figure 4B:
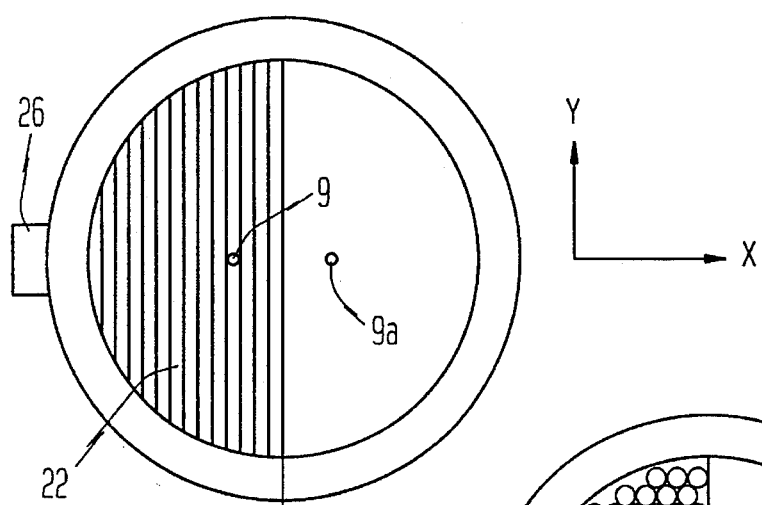
Figure 4C:
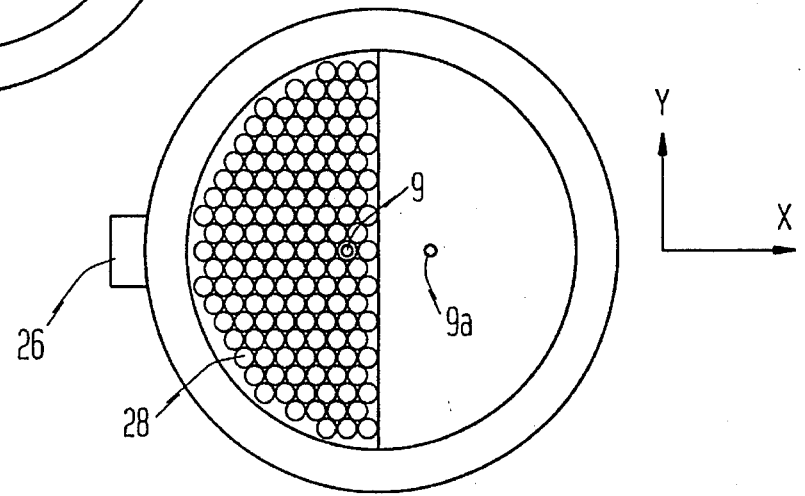

FIG. 4b illustrates an embodiment whereby light channels 22 are partitions that parallel the partitions at the center of the scatter grid 15. The illustrated arrangement of light channels 22 makes it possible to precisely position the cassette at an angle to the apparatus. The light channels 22 in the embodiment illustrated in FIG. 4c are in the form of cylinders perpendicular to the first plane of orientation. This embodiment allows particularly precise alignment. A honeycomb arrangement is also possible as an alternative.

One advantage of the present invention is that an X-ray cassette can at any time be precisely positioned in relation to the mobile apparatus. The correct orientation of the cassette is, however, very flexible in that, when the patient changes position, the cassette can always be shifted and can then be correctly positioned in relation to the overall apparatus. Another advantage of the present invention is that the dose can be kept fairly low because the radiation can be exploited very efficiently in conjunction with the scatter grid. The image will also be satisfactory. Very little time is needed to position the cassettes because the correct position will be immediately apparent.

Another advantage is that the shaft ratio of light channels 22 equals that of the scatter grid.

Although the present invention has been specified herein with reference to only a few embodiments, by way of example, many alternatives are possible. It is for example possible to employ an infrared or ultrasonic pointer instead of a laser. The beam will in that event be intercepted by an appropriate sensor which develops an electronic signal.

It can also be of advantage, in order to determine whether the laser beam is shining on the positioning device, for the window to be partly reflecting or diffusing. Further, the positioning device can emit sounds instead of, or in addition to visible signals. It is also possible to mount the positioning device directly on a conventional X-ray cassette instead of on a holder.

Figure 5:
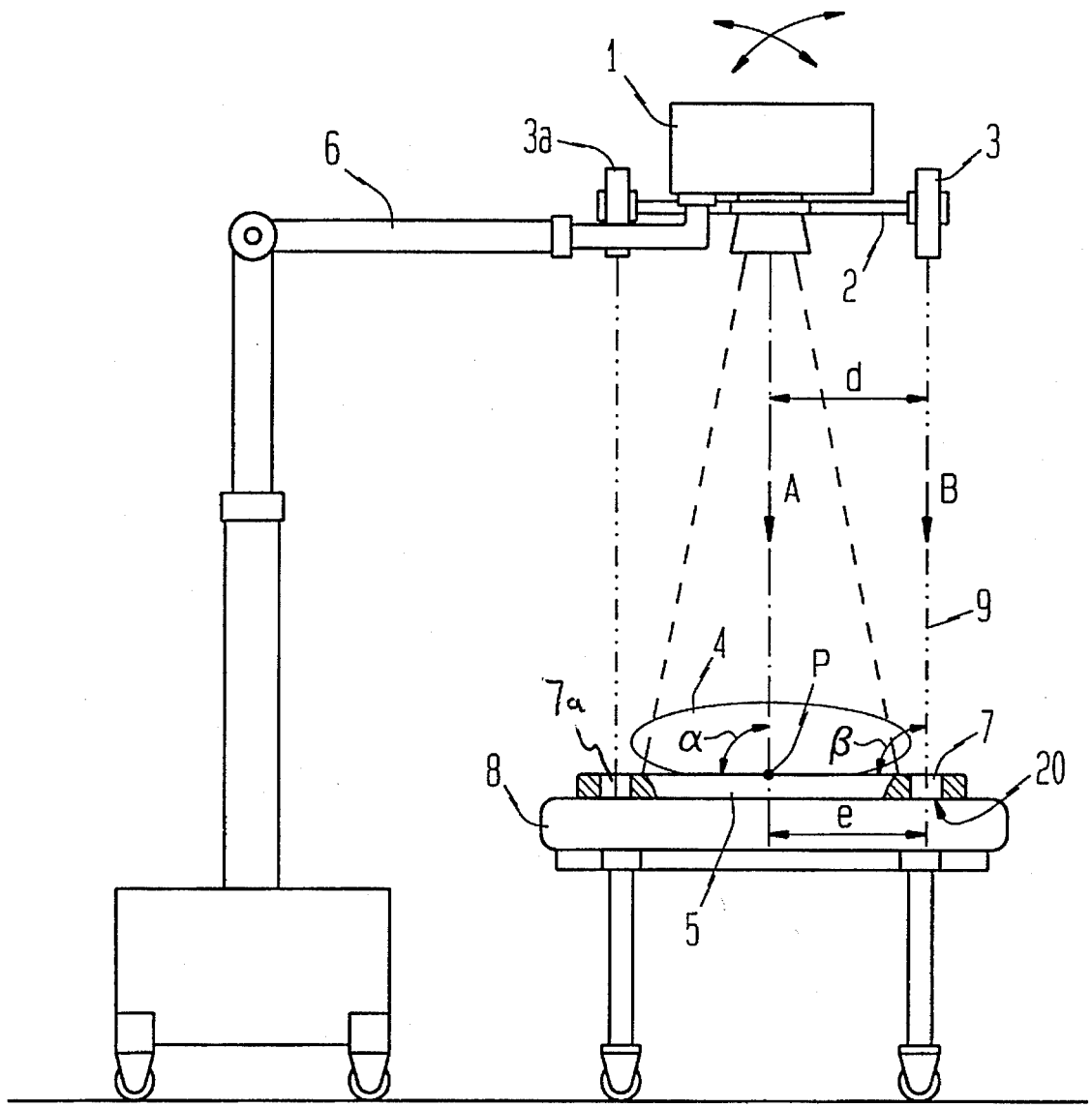
FIG. 5 shows a modification of the X-ray apparatus of FIG. 1, which incorporates two signal emitters and two positioning devices.

It is also of advantage to employ two signal emitters and two positioning devices as shown in FIG. 5. The positioning devices 7 and 7a can be mounted at diagonally opposite corners of the cassette. The signal emitters 3 and 3a will in this event be positioned opposite the X-ray source separated by a distance equal to that between the two sensors. For cassettes of various sizes, grid marks can be provided on the telescoping sections of the two signal emitters 3 and 3a to ensure that the distance between the two emitters is appropriate for the cassette. The axis of the X-rays will accordingly also be directed at the center of the cassette.

There has thus been shown and described a novel method of and device for positioning an X-ray cassette which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In apparatus for positioning an X-ray cassette in relation to an X-ray source that emits X-rays in a specific preferred direction (A), wherein another radiation source emits a secondary beam parallel to the preferred direction at a specific distance (d) therefrom, the improvement comprising position detecting means secured to the cassette for producing a signal indicating whether the angle of incidence of the secondary beam exceeds a specific threshold angle ($\theta$) with respect to the normal to the cassette, said position detecting means including several adjacent light channels, each with a specific available cross-section and through each of which incident radiation can be conducted from an entrance to an exit, whereby the light can arrive at the exit only when the angle of incidence of the light does not exceed said specific threshold angle ($\theta$).

2. The apparatus defined in claim 1, wherein the other radiation source is a laser.

3. The apparatus defined in claim 1, wherein the position detecting means include two mutually perpendicular reflective surfaces that deflect the incident light 180°.

4. The apparatus defined in claim 1, wherein the light channels parallel a plurality of partitions in a scatter grid accommodated in the cassette.

5. The apparatus defined in claim 4, wherein the shaft ratio of the scatter grid equals that of the light channels.

6. The apparatus defined in claim 1, wherein the distance (e) between the position detecting means and the center of the cassette equals the distance between the source of the secondary beam and the source of X-rays.

7. The apparatus defined in claim 1, wherein the light channels are demarcated by adjacent partitions.

8. The apparatus defined in claim 1, wherein the light channels are adjacent cylinders.

9. The apparatus defined in claim 3, wherein the positioning means includes a matte-surfaced disk above the second reflective surface, whereby the beam intercepted by the position detecting means impinges on the disk only when the beam's angle of incidence does not exceed said specific threshold angle.

10. The apparatus defined in claim 1, wherein two of said position detecting means are each secured to diagonally opposite corners of the cassette.

11. The apparatus defined in claim 10, wherein two other sources of beams are provided, said other sources being spaced apart the same distance as said two position detecting means.

* * * * *